Figure 4:
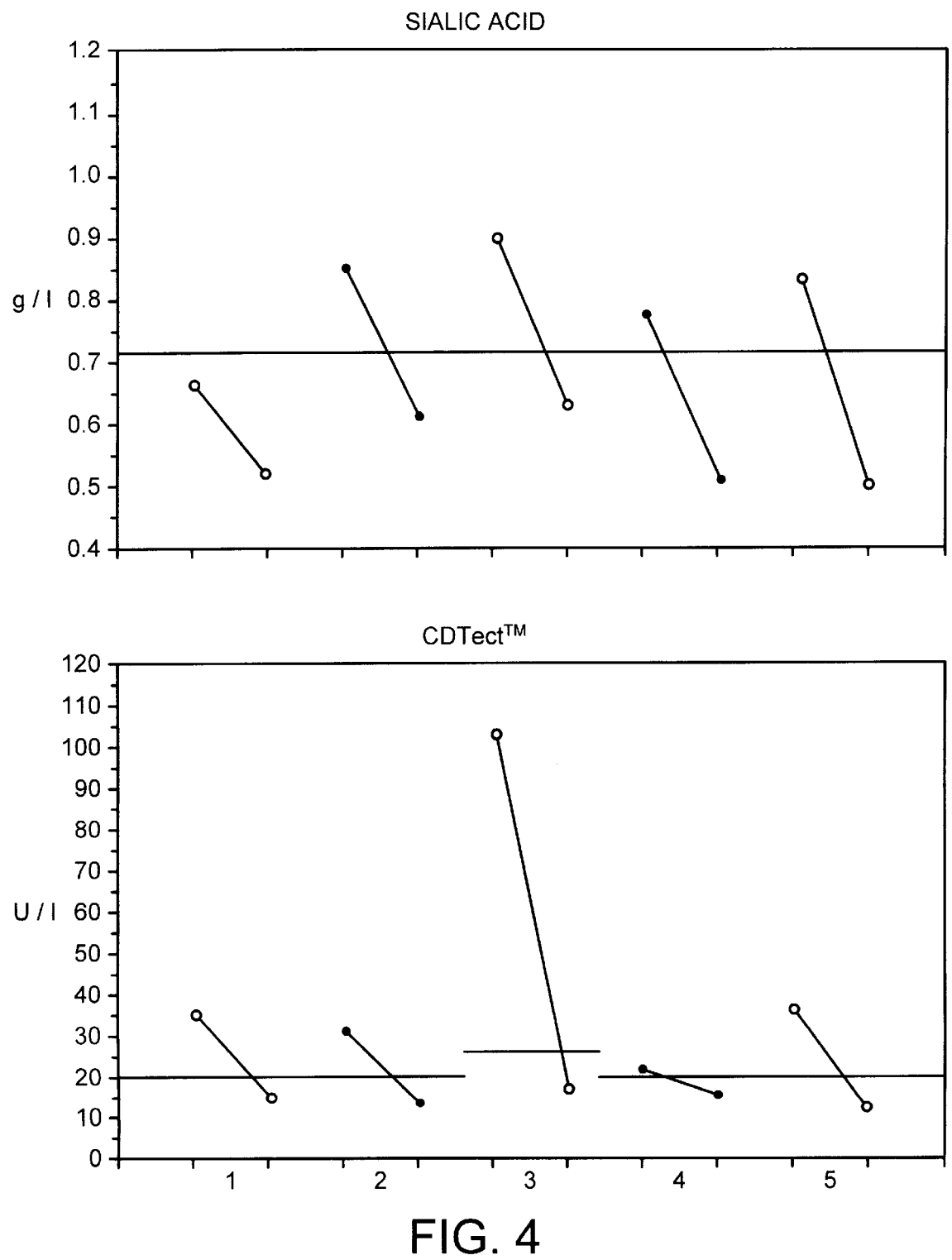

United States Patent [19]
Sillanaukee et al.

[11] Patent Number: 6,054,322
[45] Date of Patent: *Apr. 25, 2000

[54] USE OF SIALIC ACID DETERMINATION FOR DETERMINING ALCOHOL CONSUMPTION

[75] Inventors: Pekka Sillanaukee, Uppsala, Sweden; Kaija Seppä, Tampere, Finland; Ola Mårtensson, Knivsta, Sweden

[73] Assignee: Axis-Shield ASA, Oslo, Norway

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,894
[22] PCT Filed: Jun. 7, 1995
[86] PCT No.: PCT/SE95/00672
§ 371 Date: Feb. 23, 1997
§ 102(e) Date: Feb. 23, 1997
[87] PCT Pub. No.: WO95/33993
PCT Pub. Date: Dec. 14, 1995

[30] Foreign Application Priority Data

Jun. 7, 1994 [SE] Sweden .................................. 9401975

[51] Int. Cl.[7] .......................... G01N 33/48; G01N 33/49; G01N 33/493
[52] U.S. Cl. ................................. 436/93; 436/63; 436/87; 436/94; 436/96; 436/129; 436/131; 436/132
[58] Field of Search .................................. 436/63, 66, 67, 436/87, 93, 94, 96, 129, 131, 132

[56] References Cited

U.S. PATENT DOCUMENTS

| | | |
|---|---|---|
| 4,463,098 | 7/1984 | Hoberman .................................. 436/67 |
| 4,626,355 | 12/1986 | Joustra et al. ....................... 436/161 X |
| 5,066,583 | 11/1991 | Mueller .................................. 436/63 X |
| 5,126,271 | 6/1992 | Harasymiw .............................. 436/71 |

OTHER PUBLICATIONS

W.R. Klemm et al. *J. Neurosci. Res.* 1978, 3, 341–351.
K. Taniuchi et al. *Rinsho Kagaku* 1979, 7, 403–410.
H. Levinsky et al. *Acta Haemat.* 1980, 64, 276–280.
F.W. Kuntsmann *Dtsch. Gesundheitwes.* 1980, 35, 1685–1688.
H. Stibler et al. *Alcoholism Clin. Exp. Res* 1981, 5, 545–549.
J. Mathew et al. *Alcohol* 1988, 5, 499–503.
Y. Kohgo et al. *Igaku to Ayumi* 1990, 154, 853–858.
M.R. Lakshman et al. *Alcoholism Clin. Exp. Res.* 1993, 17, 466.
G. Lindberg et al. *Atherosclerosis* 1993, 103, 123–129.
G. Bollmann *Eur. J. Clin. Chem. Clin. Biochem.* 1994, 32, 37–40.
Alcoholin Metabolism, 1984, Yutaka Kohgo et al: *Metabolism of Serum Sialic Acid in Habitual Alcoholics*, pp. 58–61, fig. 1.
Drug and Alcohol Dependence, vol. 26, 1990, L. Cherian et al: *Effect of Acute Injections of Ethanol on Lipid and Protein–Bound Sialic Acid in Mice of Different Ages*, pp. 29–34.

*Primary Examiner*—Arlen Soderquist
*Attorney, Agent, or Firm*—Dinsmore & Shohl I

[57] ABSTRACT

A method for the determination of an individual's alcohol consumption, characterized in comprising the steps: i) determining the level of sialic acid in a body fluid sample from the individual; ii) comparing the level found in step (i) with the level for the normal population, an increased level being an indication of an increased alcohol consumption relative to the consumption (per individual) of the normal population.

15 Claims, 5 Drawing Sheets

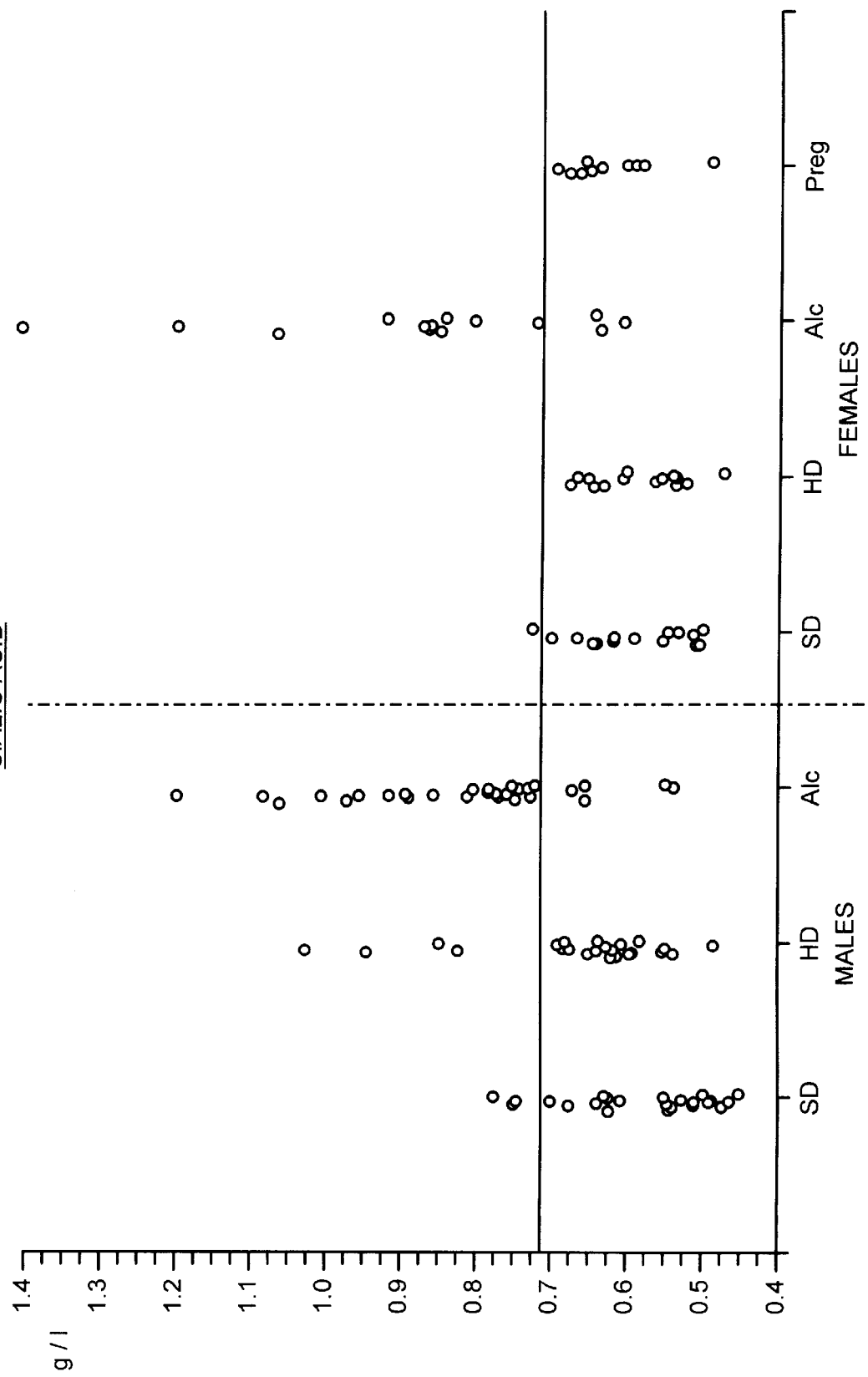

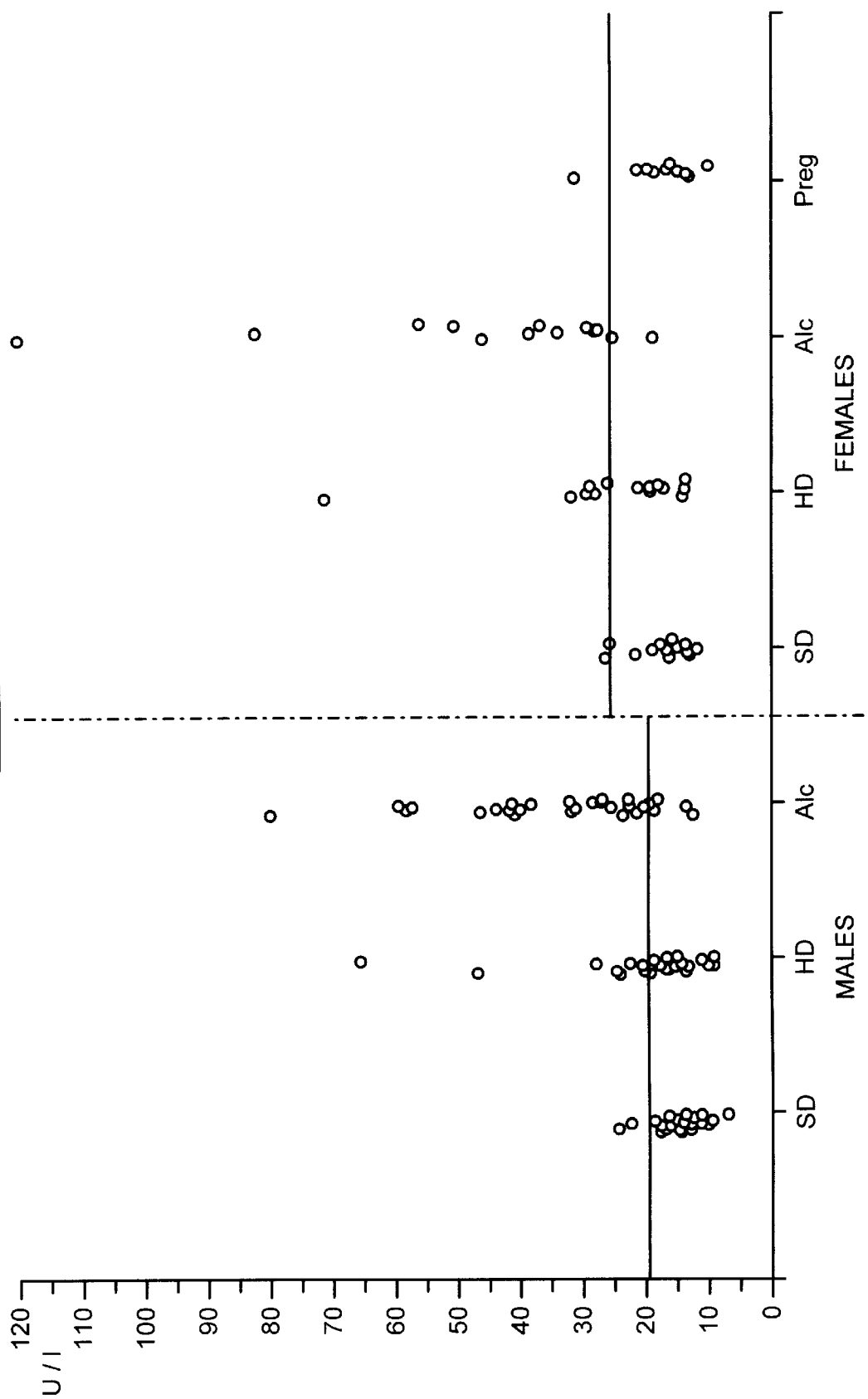

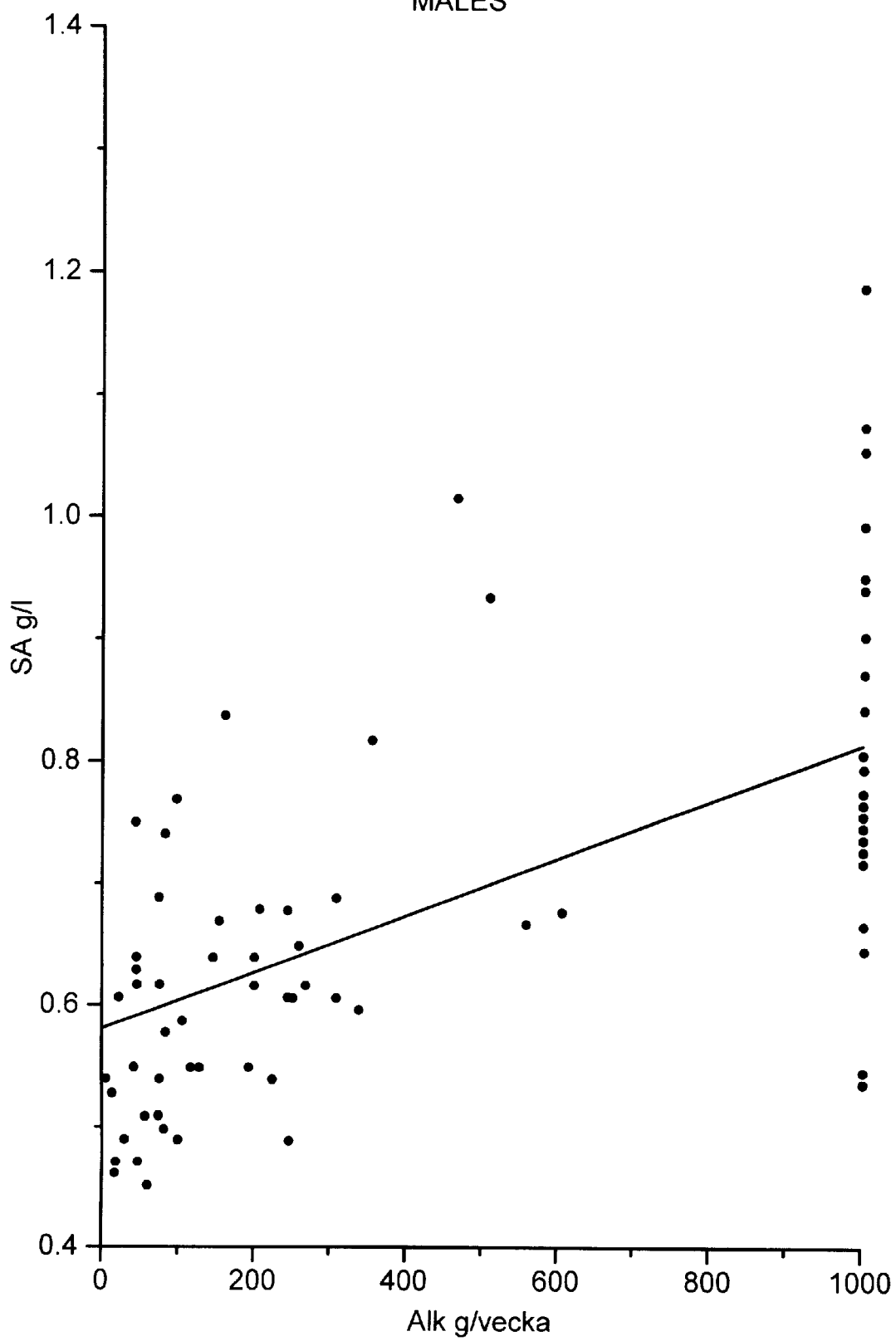

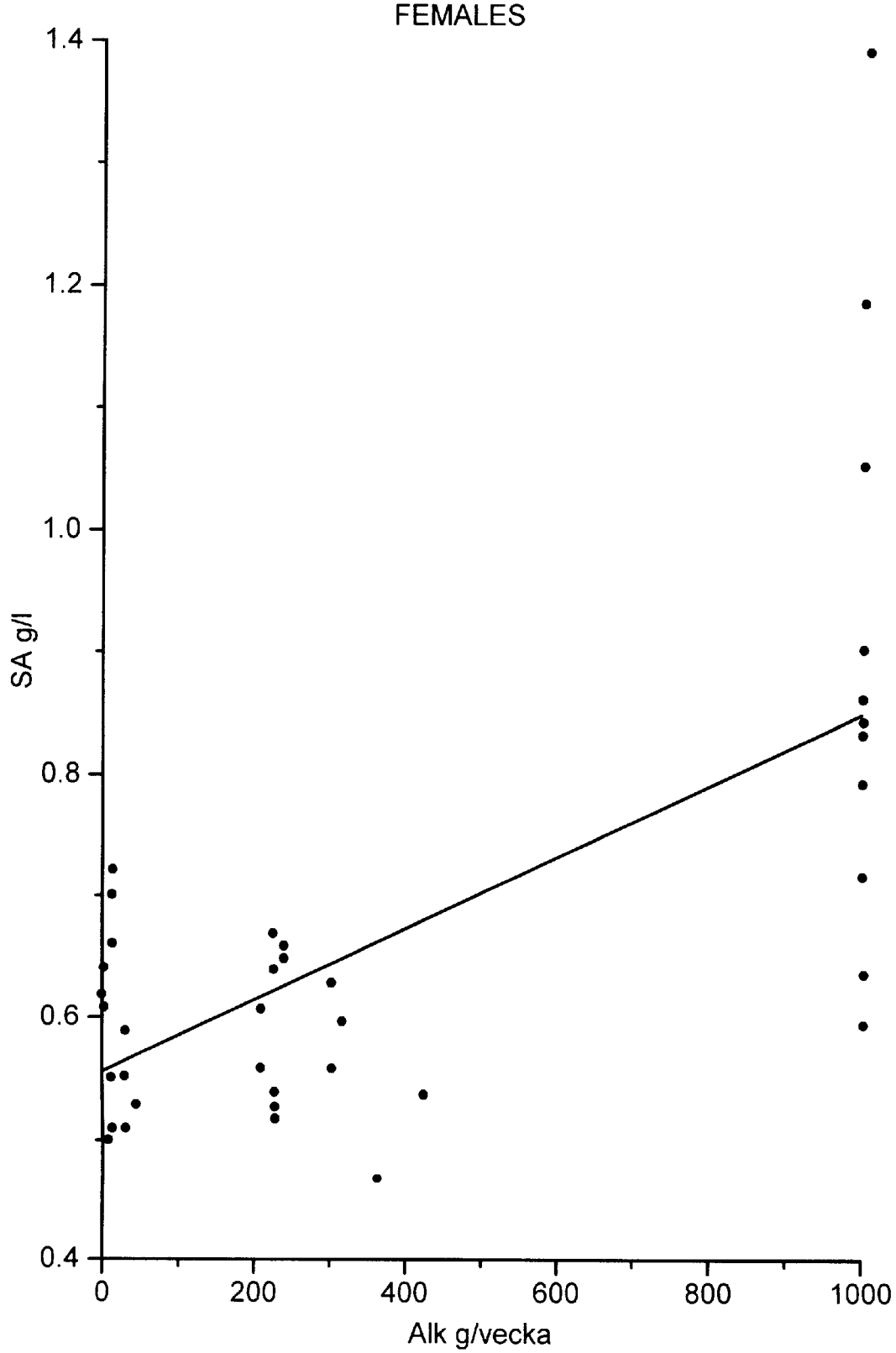

USE OF SIALIC ACID DETERMINATION FOR DETERMINING ALCOHOL CONSUMPTION

The present invention concerns sialic acids, in particular N-acetylneuraminic acid (NANA), as a marker for detecting/determining frequent alcohol consumption/ prolonged alcohol consumption and/or alcohol abuse and/or alcohol habits.

By alcohol is meant ethanol.

The measurement of sialic acid and its clinical significance has been reviewed several times (e.g. Waters et al., Ann. Clin. Biochem. 29 (1992) 625–537).

Sialic acid is the common name for compounds derived from neuraminic acid. These compounds have the formula:

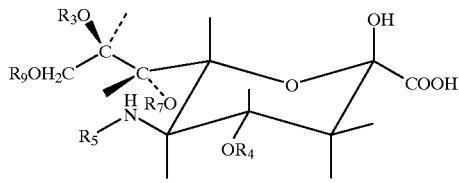

In natural sialic acids $R_4$ and $R_7$ are H— or $CH_3CO$—; $R_5$ is $CH_3CO$— or $HOCH_2CO$—; $R_8$ is H—, $CH_3CO$—, $CH_3CH(OH)CO$—, $CH_3$— and $SO_3H$—; and $R_9$ is H—, $CH_3CO$—, $CH_3CH(OH)CO$— or $PO_3H_2$—. The most abundantly present sialic acids in living material is N-acetylneuraminic acid (NANA) in which $R_5$ is $CH_3CO$— and $R_{4,7,8,9}$ are H—.

Sialic acids have been detected in several biological fluids, for instance blood, plasma/serum and urine. Sialic acids may exist as free forms or as terminal residues in oligosaccharide chains that in turn may be linked to proteins/ peptides and lipids (gangliosides). The normal level in serum/plasma is 2–3 mmol/L (600–900 mg/ml, free plus bound sialic acids) with the free form only constituting 0.5–1 μmol/L and the lipid associated forms about 10 μmol/L. In urine the normal level varies with age and about 30–50% of the total level relates to free sialic acids.

Increased sialic acid levels in body fluids have been associated with several different diseases (renal diseases, various central nervous system disorders, bacterial infections, Crohn's disease, psoriasis, arthritis etc).

The increased plasma/serum levels of certain carbohydrate deficient transferrins (CDTs=asialo-, monosialo- and disialotransferrins) have been associated with prolonged alcohol consumption (EP-A-172,217 and WO-A-9119983) and alcohol abuse. The measurement of the relevant CDTs has resulted in somewhat complicated assay procedures requiring separation of asialo-, monosialo- and disialotransferrins from the other transferrins. It has therefore been a common desire to look for other markers of increased alcohol consumption.

It has earlier been found that that the range for sialic acid serum levels of alcoholics (68.1±14.6 mg/dl) fully encompasses the range for non-alcoholics with a strong tendency for the non-alcoholics to appear in the lower part (63.5±6.9 mg/dl) of the range for the alcoholics (Kougo, Alcohol and Metabolism 3 (1984) 58–62). This observation makes sialic acid useless as a clinical relevant marker for alcohol abuse. The author Kuogo himself indicates in last paragraph of the article that it is unlikely that there is a true connection between raised serum levels and alcohol drinking (". . . other factors must be considered, such as difference in sugar protein-producing cells (tissues), starvation before hospitalization, infection etc . . . ").

A first objective of the present invention is to provide simpler methods for detecting/determining an individual's prolonged alcohol consumption, alcohol abuse and/or frequent alcohol intake.

A second objective is to provide an alternative marker for alcohol abuse and/or prolonged alcohol consumption and/or frequent alcohol intake.

Thus the invention is a method for the determination/ detection of prolonged alcohol consumption of an individual. The method is characterized by comprising the steps
 i. determining the level of sialic acid in a body fluid sample from the individual,
 ii. comparing the level found in step i with the level for the normal population, an increased level being an indication of an increased alcohol consumption of the individual relative the consumption (per individual) of the normal population.

In the alternative an increased level may be correlated to alcohol abuse or frequent alcohol intake of the individual. A normal value indicates that the individual does not have the habit of drinking alcohol.

At the priority date it was preferred to determine and correlate the total amount of sialic acids although it can not be excluded that the analogous correlation is at hand for free sialic acids and/or protein bound and/or lipid bound forms of sialic acids. The large deviation from the normal CDT value found in comparison with the relatively low portion present as free sialic acids indicates that the correlation is at hand at least also for bound forms of sialic acids.

The individual is normally a human being. The body fluid sample is preferably a blood sample, such as plasma, serum or whole blood sample or any other sample that contains any of the above-mentioned forms of sialic acids, the concentration of which correlates to the above-mentioned aspects of alcohol consumption. Potentially measurement may also be performed in urine.

The specific method used for measuring sialic acids may be any of the large variety of available methods for this analyte including methods to be developed in the future. See for instance Waters et al., Ann. Clin. Biochem. 29 (1992) 625–37, with particular emphasis of colourimetric, fluorometric, enzymatic and chromatographic methods. Recently, antibodies (monoclonals) specific for free NANA have been developed (Kawamura et al., Biochim. Biophys. Acta 1033 (1990) 201–6) which will open up the use of immunological assays too.

Experimentals

METHODS:

Sialic acid was determined by an enzymatic test (Boehringer Mannheim, Germany). Carbohydrate deficient transferrins (CDTs=asialo-, monosialo- and disialotransferrin) were measured by CDTect® (Pharmacia Diagnostics AB). C-reactive protein (CRP) was measured by an immunoturbidometric assay (Orion Diagnostics).

The sialic acid assay used measures the total amount of sialic acid, that is free sialic acid and sialic acid bound to entities such as proteins and lipids. The test principle comprises release of bound sialic acid by neuraminidase, cleavage of the sialic acid into N-acetylmannosamine and pyruvate by the use of AcNeu aldolase, oxidation of pyruvate by pyruvate oxidase which gives dihydrogen peroxide. The amount of dihydrogen peroxide formed is a function of sialic acid and is quantitated by conversion to a dye through oxidation by peroxidase in the presence of 4-aminopyridine and N-ethyl-N-2-hydroxymethyl-3-toluidine.

The test principle of CDTect comprises an ion exchange chromatographic separation of asialo-, monosialo- and disialotransferrins from the other transferrins whereupon asialo-, monosialo- and disialotransferrins are measured by a sandwich immuno assay. The immunoassay step comprises adsorption of the separated isotransferrins to an adsorbent carrying anti-transferrin antibodies followed by quantitation of the adsorbed transferrins by a labelled anti-transferrin antibody.

SUBJECTS:

Males: Sera (after an overnight fast) were collected and stored at −70° C. until analysis. Controls were 26 healthy 40 to 45 years old male subjects. They all reported consumption of less than 105 g absolute ethanol per week. The mean ± SD alcohol consumption was 42±34 g per week. Heavy drinkers were 28 male subjects, 40 to 45 years old, who reported an alcohol consumption of 50–600 g absolute ethanol per week. The group was classified using Malmo modified Michigan Alcoholism Screening Test. Alcoholics were 28 male subjects (age range 27–63 years old) with well-documented history of chronic alcoholism who were reporting for a detoxification at a treatment center. Their weekly self-reported alcohol consumption was more than 1000 g of absolute ethanol. None of the subjects included to the study reported or had any clinical signs of liver disease (jaundice, ascites or peripheral oedema).

Females: Sera (taken after an overnight fast) were collected and stored at −70° C. until analysis. Controls were 15 healthy 45 years old female subjects. They all reported consumption of less than 50 g absolute ethanol per week. The mean ± SD alcohol consumption was 16±13 g per week. An additional group of 10 pregnant women in the 16th week of pregnancy was included. Self-reported alcohol consumption was not available. Heavy drinkers were 14 female subjects 45 years old who reported an alcohol consumption between 210–420 g absolute ethanol per week. Alcoholics were 14 females (age range 30–45 years) with well-documented history of chronic alcoholism who were reporting for a detoxification at a treatment center. Their weekly self-reported alcohol consumption was more than 1000 g of absolute ethanol. None of the subjects included into the study reported or had any clinical signs of liver disease (jaundice, ascites, peripheral oedema).

Follow up: Sera were collected from five male and one female patients at arrival to the hospital and after 12 weeks follow up. The changes of sialic acid values were compared to changes in CDT values.

Results

The values of sialic acid and CDTs in the different studied groups are shown in FIG. 1 and 2, respectively.

The mean values of sialic acid in the controls (males and females) were 0.58±0.09 g/l and 0.59±0.07 g/l, respectively. The mean values in the alcoholics (males and females) were 0.81±0.15 g/l and 0.87±0.22 g/l, respectively. Using 0.71 g/l as cut-off, the sensitivity of sialic acid as a marker to detect alcoholics was 82% (23/28) among males and 79% (11/14) among females. Using the same limits, the specificity was 88% (23/26) among males and 93% (14/15) among females.

For CDT the sensitivity was 82% (23/28) among males and 86% (12/14) among females and the specificity was 92% (24/26) and 93% (14/15), respectively.

There was no correlation between the serum levels of sialic acid or CDTs and CRP. The comparison between self-reported alcohol consumption and sialic acid is shown in FIG. 3. The correlations were statistically significant both for men (r=0.64, p<0.001) and women (r=0.68, p z 0.001).

FIG. 4 shows the reduction of sialic acid and CDT values after 12 weeks follow up. All patients had a clear reduction of the concentrations of sialic acid and CDTs.

Conclusion

The results of the study indicate that alcohol consumption and serum levels of sialic acid have a strong and positive correlation with each other. The alcohol abusers had a statistically and significantly elevated serum concentration of sialic acid. The relationship found for sialic acid in the present study can not be explained by acute phase reactions, liver diseases or other known diseases. As compared to the best traditional marker of alcohol consumption, CDT and sialic acid seems to have similar sensitivities and specificities. The serum level of sialic is normalised during alcohol withdrawal.

We claim:

1. A method for discriminating individuals consuming over about 1000 g of alcohol per week from those consuming less than about 100 g of alcohol per week, comprising measuring a sialic acid level in a body fluid sample of the individual, wherein the body fluid is of a type containing sialic acid levels reflecting alcohol consumption, and comparing the measured level to a value above which there is a significant probability that the individual is consuming over 1000 g of alcohol per week.

2. A method according to claim 1, wherein the total amount of sialic acid in the sample is determined.

3. A method according to claim 1, wherein bound sialic acid in the sample is determined.

4. A method according to claim 1, wherein the sample is a blood sample.

5. A method according to claim 1, wherein the sample is a serum sample.

6. A method for discriminating male individuals consuming over about 1000 g of alcohol per week from those consuming less than about 600 g of alcohol per week, comprising measuring a serum sialic acid level in a body fluid sample of the male individual, wherein the body fluid is of a type containing sialic acid levels reflecting alcohol consumption, and comparing the measured level to a value above which there is a significant probability that the individual is consuming over 1000 g of alcohol per week.

7. A method according to claim 6, wherein the total amount of sialic acid in the sample is determined.

8. A method according to claim 6, wherein bound sialic acid in the sample is determined.

9. A method according to claim 6, wherein the sample is a blood sample.

10. A method according to claim 6, wherein the sample is a serum sample.

11. A method for discriminating female individuals consuming over about 1000 g of alcohol per week from those consuming less than about 420 g of alcohol per week, comprising measuring a sialic acid level in a body fluid sample of the female individual, wherein the body fluid is of a type containing sialic acid levels reflecting alcohol consumption, and comparing the measured level to a value above which there is a significant probability that the individual is consuming over 1000 g of alcohol per week.

12. A method according to claim 11, wherein the total amount of sialic acid in the sample is determined.

13. A method according to claim 11, wherein bound sialic acid in the sample is determined.

14. A method according to claim 11, wherein the sample is a blood sample.

15. A method according to claim 11, wherein the sample is a serum sample.

* * * * *